United States Patent [19]

Diaz

[11] Patent Number: 5,338,301
[45] Date of Patent: Aug. 16, 1994

[54] EXTENDABLE BALLOON-ON-A- WIRE CATHETER, SYSTEM AND TREATMENT PROCEDURE

[75] Inventor: Juan-Carlos Diaz, Miami, Fla.

[73] Assignee: Cordis Corporation, Miami Lakes, Fla.

[21] Appl. No.: 112,684

[22] Filed: Aug. 26, 1993

[51] Int. Cl.5 .................. A61M 29/00; A61B 6/00
[52] U.S. Cl. ..................... 604/96; 606/194; 128/657
[58] Field of Search ............... 604/53, 96–103; 606/192, 194; 128/656–658

[56] References Cited

U.S. PATENT DOCUMENTS

| | | | |
|---|---|---|---|
| 4,445,892 | 5/1984 | Hussein et al. | 604/101 |
| 4,616,653 | 10/1986 | Samson et al. | 128/657 |
| 4,655,746 | 4/1987 | Daniels et al. | 604/101 |
| 4,827,941 | 5/1989 | Taylor et al. | 128/657 |
| 4,846,174 | 7/1989 | Willard et al. | 128/344 |
| 4,846,193 | 7/1989 | Tremulis et al. | 128/772 |
| 4,867,742 | 9/1989 | Calderon | 604/101 |
| 4,958,634 | 9/1990 | Jang | 604/101 |
| 4,973,305 | 11/1990 | Goltzer | 604/101 |
| 5,000,743 | 3/1991 | Patel | 604/101 |
| 5,026,355 | 6/1991 | Sweeney et al. | 604/243 |
| 5,102,390 | 4/1992 | Crittenden et al. | 604/96 |
| 5,195,535 | 3/1993 | Shank | 128/657 |
| 5,205,822 | 4/1993 | Johnson et al. | 604/96 |
| 5,222,966 | 6/1993 | Perkins et al. | 604/96 |
| 5,247,942 | 9/1993 | Prather | 128/657 |

Primary Examiner—C. Fred Rosenbaum
Assistant Examiner—Frank Wilkens
Attorney, Agent, or Firm—Lockwood, Alex, Fitzgibbon & Cummings

[57] ABSTRACT

An extendable balloon-on-a-wire catheter is provided which includes a telescoping exchange core wire mounted along the inside lumen of the longitudinal tube of the balloon-on-a-wire assembly. In the preferred embodiment, the exchange core wire is mounted within a hypodermic tube secured to the core wire of the balloon-on-a-wire assembly. A multiple component system includes this balloon-on-a-wire assembly together with an over-the-wire catheter which slidably passes over the elongated body of the balloon-on-a-wire assembly. Preferably, the relative sizing of these components of the system is such that the over-the-wire catheter does not pass over the balloon of the balloon-on-a-wire assembly. In a treatment procedure, the balloon-on-a-wire assembly achieves dilation of a lesion or a stenosis, after which it is moved somewhat distally to clear the stenosis. When the over-the-wire catheter is used, it is slidably moved over the balloon-on-a-wire assembly until its treatment location reaches the stenosis. During the procedure, the exchange core wire can be telescopically extended to a length such that the surgeon can readily grasp the balloon-on-a-wire assembly or its exchange core wire during manipulation of the over-the-wire catheter.

23 Claims, 2 Drawing Sheets

FIG. 1   FIG. 2A   FIG. 2

EXTENDABLE BALLOON-ON-A- WIRE CATHETER, SYSTEM AND TREATMENT PROCEDURE

BACKGROUND AND DESCRIPTION OF THE INVENTION

This invention generally relates to percutaneous transluminal treatments and devices therefor. More specifically, the invention relates to improvements in catheter systems and treatment procedures including angioplasty for treating stenoses in blood vessels and other vessels of living bodies. A balloon-on-a-wire catheter device operates both as a balloon catheter and as a guidewire, which balloon-on-a-wire catheter also has a telescoping extension assembly therewithin. When the extension assembly is extended, the balloon-on-a-wire catheter operates as an extended guidewire that permits an over-the-wire percutaneous transluminal catheter to be guided therealong for treatments such as angioplasty treatment with a balloon having an expanded radial size larger than that of the balloon-on-a-wire catheter.

Percutaneous balloon angioplasty procedures are therapeutic medical treatments that can increase blood flow through a blood vessel or other body passageways exhibiting undesirable occlusions. As is well known, an elongated catheter having a deflated balloon at its distal end is guided through the body, such as through a patient's cardiovascular system to the coronary artery of the heart. Then, the balloon is inflated by a source of fluid under pressure originating outside of the body in order to compress deposits or plaque or undesired protrusions. For example, by this procedure, plaque can be compressed to an arterial wall, thereby dilating the stenosis or lesion.

Often balloon catheters cannot be negotiated easily through branching blood vessels to reach the location of the stenosis. Typically, surgeons assist in maneuvering these catheters by first inserting a more maneuverable guidewire through the vessel and branches and to the stenosis location. Then a balloon catheter is slidably inserted over the guidewire to and through the stenosis. After balloon inflation, the catheter and guidewire are removed. A limitation of this approach is that, in order to permit catheterization to be initiated, the stenosis must be open enough to permit insertion of the balloon catheter therethrough. Patients who exhibit particularly tight stenoses typically are obliged to undergo the risk and expense of heart bypass surgery, for example. At other times, the stenosis is such that, after insertion of a first balloon catheter and most likely after catheterization has been effected with this balloon, the surgeon determines a different catheter is needed for the particular procedure. Thus, in certain procedures, it is necessary to exchange catheters to treat a single lesion and/or multiple lesions within the same vessel. In those instances, it is desirable to avoid having to retract the guidewire tip from its position distal of the lesion before the time when treatment is completed. For example, if the guidewire is removed from (passed proximally of) the lesion, the passageway (which may already be very limited in size) may close due to a blood vessel spasm so that the guidewire cannot again safely be pushed through the lesion.

Extendable guidewires have been suggested for introducing a dilatation catheter into a cardiovascular system. Such an extendable guidewire has a guidewire section and an extension section with a connection for joining the two sections together. The guidewire section is used for positioning the catheter within the subject, and the extension section is used to extend the length of the guidewire in order to exchange catheters. Included in this regard are U.S. Pat. No. 4,827,941 and No. 4,846,193, the latter guidewire having first and second interfitting sections movable between an extended and a retracted position.

Approaches such as those of U.S. Pat. No. 4,846,174 and No. 5,102,390 call for insertion of a guidewire so that its tip is distal of the lesion, followed by insertion of a balloon catheter to the lesion location. If the lesion is too occluded to permit insertion of the uninflated balloon catheter, approaches such as these call for removal of the guidewire through the lumen of the balloon catheter while holding the balloon catheter on the proximal side of the stenosis. The surgeon then inserts a microdilation probe, dilating guidewire, or similar device through the lumen of the balloon catheter and to the lesion. The balloon of the probe or dilating guidewire is inflated in order to create an opening sufficiently large to permit insertion of the balloon catheter therethrough to effect further dilation of the lesion.

In summary, the present invention provides a balloon-on-a-wire catheter having an extension assembly within its lumen, the extension assembly having an elongated core wire which can be pulled out of the lumen to, in effect, provide an elongated guidewire that will accept an over-the-wire percutaneous transluminal balloon catheter. With this structure, the balloon-on-a-wire catheter can be transluminally threaded to the location of a lesion by the use of a suitable control handle or the like. Thereafter, the control handle is removed while the balloon-on-a-wire catheter remains placed at the lesion in order to thereby gain access to the proximal end of the extendable core wire which is then pulled and extended. An over-the-wire catheter can then be slid over the extended core wire and the balloon-on-a-wire catheter for treatment as needed in addition to that provided by the balloon-on-a-wire catheter.

It is a general object of the present invention to provide an improved balloon-on-a-wire catheter which is extendable, a kit of parts including same and an over-the-wire catheter, and a treatment procedure utilizing same.

Another object of the present invention is to provide an improved balloon-on-a-wire catheter which is extendable in a proximal direction without disturbing the positioning of the distal end of the balloon-on-a-wire catheter and without requiring attachment of an extending member thereto.

Another object of the present invention is to facilitate a percutaneous transluminal treatment procedure wherein the number of steps required to perform an angioplasty procedure is reduced in an arrangement that avoids having a guidewire type of member pass distally of a lesion more than once during the entire procedure.

Another object of this invention is to improve the ability for a balloon-on-a-wire catheter to be used both as a stenosis treating device and as a guidewire for another catheter device without requiring any additional components or attachments.

These and other objects, features and advantages of this invention will be clearly understood through a consideration of the following detailed description.

BRIEF DESCRIPTION OF THE DRAWINGS

The invention will be further elucidated in the following description with reference to the drawings in which.

DESCRIPTION OF THE PARTICULAR EMBODIMENTS

Figures 1, 2A:
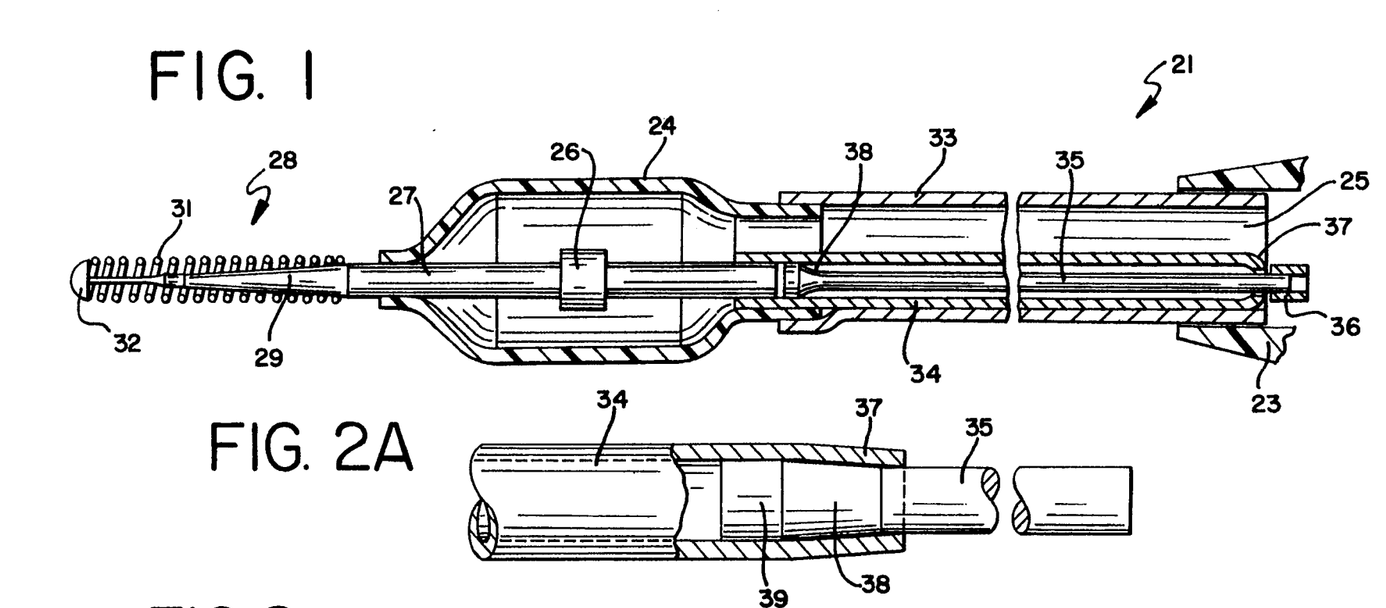
FIG. 1 is a longitudinal view, partially in cross-section, illustrating an extendable balloon-on-a-wire catheter in accordance with the present invention.
FIG. 2A is an enlarged detail view, partially in cross-section, showing a preferred movement-limiting feature of the catheter as extended.

The present invention includes an extendable fixed wire percutaneous transluminal catheter for angioplasty, generally designated as 21 in FIG. 1. Fixed wire or balloon-on-a-wire catheter 21 is especially suitable for use in working combination with an over-the-wire catheter such as the percutaneous transluminal catheter for angioplasty, generally shown at 22 in FIG. 7. The profile of the extendable balloon-on-a-wire catheter is generally the same as that of a standard guidewire, permitting comparable maneuverability in order to access the stenosis. For example, the extendable balloon-on-a-wire catheter is attachable to a steering device which permits the surgeon to impart desired rotation, torque and maneuverability by movement of the proximal end of the extendable catheter for its placement as desired within the body cavity.

A balloon 24 is positioned near the distal end of the balloon-on-a-wire catheter. Steering device 23, at the proximal end of the catheter 21, facilitates connection to equipment for carrying out desired medical procedures. For example, in addition to serving its steering and maneuvering function, the steering device also serves as a manifold to communicate pressurized fluid to and through the catheter 21, the fluid passing through passageway 25 of the catheter 21. This pressurized fluid, when flowing in the distal direction, inflates the balloon 24 to achieve dilation or predilation as needed. In this regard, a radiopaque band or marker 26 can be provided at a suitable location, such as the illustrated axial center of the balloon 24, in order to assist the surgeon in dilating at the desired location.

Catheter 21 also includes a core wire 27 having a flexible tip 28 at the distal end thereof. Included at the distal tip portion is a tapered length 29 of the core, shown having a coil 31 secured thereto and to a generally hemispherical weld 32 at its distal tip. In addition to being secured at its distal end to the core wire 27, the balloon 24 is secured at its proximal end to a fixed wire tube 33 by suitable connection such as medical grade solder, adhesive and the like. The fixed wire tube 33 has a length adequate for insertion into the desired body cavity such that its proximal end remains outside the body and connectable to the steering device 23 as generally illustrated. During use of the device, a significant distal length of the fixed wire catheter 21 remains within the body during all stages of the preferred procedures, there being no need to withdraw the fixed wire catheter until treatment has been completed.

Proximal end of the core wire 27 is permanently secured by suitable assembly techniques such as soldering, the use of medical grade adhesive, crimping, swaging, and the like, to a narrow diameter hypodermic tube or hypotube 34. The outer diameter of hypotube 34 is less than the inner diameter of the fixed wire tube 33, thereby providing the elongated longitudinal passageway 25 defined therebetween. In the illustrated preferred embodiment, substantially the entire length of the hypodermic tube 34 is secured to a circumferential portion of the longitudinal lumen of the fixed wire tube 33. Generally speaking, the hypodermic tube 34 extends throughout about the proximal ⅔ of the overall length of the fixed wire or balloon-on-a-wire catheter 21. Both the fixed wire tube 33 and the hypodermic tube 34 therewithin typically are made of metal which, in the configuration of these thin-walled tubes, presents a flexible characteristic which facilitates their torqued movement through body passageways as desired. Preferably, securement between the hypodermic tube 34 and its supportive fixed wire tube 33 is by means of a medical grade adhesive suitable for adhering two metals together, for example. The combined tubes provide an especially rigid, yet bendable section, which enhances torque application.

Slidably positioned within the hypodermic tube 34 is an elongated exchange core wire 35. Exchange core wire 35 is dimensioned to be slightly smaller than the central passageway or lumen of the hypodermic tube 34 so that exchange core wire 35 is longitudinally movable into and out of the hypodermic tube 34 in a slidable or telescoping manner. This longitudinal movement is between the retracted position illustrated in FIG. 1 and the extended position shown in FIG. 2. In this extended position, either the distal end of the exchange core wire 35 engages the proximal end of the core wire 27 or other suitable stop means. When retracted, a proximal end bead 36 can engage the hypodermic tube 34. When fully extended, the exchange core wire 35 provides a length (at times in cooperation with a proximal portion of the tube 33) that is longer than a catheter such as the over-the-wire catheter 22 so that the surgeon can control the location of the proximal end of the exchange core wire 35 after the catheter 22 is fully inserted thereover in order to maintain control of the balloon-on-a-wire catheter 21 and prevent any undesired movement of the distal end thereof, either distal movement or proximal movement.

Figure 2:
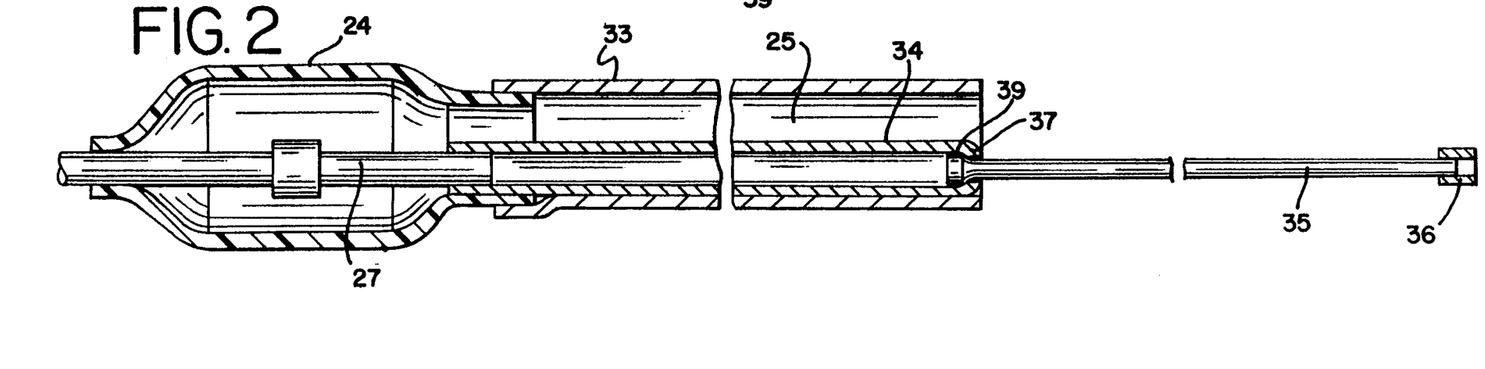
FIG. 2 is a view similar to FIG. 1, partially broken away, showing the device in an extended orientation.

Extension beyond this fully extended orientation is prevented by appropriate movement-limiting features. Illustrated in this regard is a diameter reduction area 37 to provide an opening at the proximal end of the hypodermic tube 34 which is of a reduced diameter when compared with the diameter of the hypodermic tube located distally thereof. In addition, exchange core wire 35, such at its distal end as illustrated, is enlarged or includes a stop 38. The exchange core wire 35 moves back and forth within the central passageway of the hypodermic tube 34 and through the diameter reduction area 37 until it engages the stop 38. Stop 38 is unable to pass through the diameter reduction area 37. The contact therebetween prevents separation of the exchange core wire 35 from the balloon-on-a-wire catheter and also secures the exchange core wire in its extended position during medical procedures such as those discussed herein.

With reference to the embodiment illustrated in FIG. 2A, the stop 38 and the diameter reduction area 37 engage to impede relative movement between the two during insertion or removal of a device such as catheter 22. A preferred manner of forming the diameter reduction area 37 is to practice swaging in order to reduce its diameter. For example, a hypodermic tube having an outer diameter of 0.014 inch and an inner diameter of 0.0105 inch is inserted into a die and the tube is swaged to cause the inner diameter to decrease by approximately 0.001 inch. A typical swage in this regard will have a length of about 0.25 inch. Correspondingly, stop 38 can be formed by grinding the exchange core wire material along substantially all of its length while forming a frusto-conically shaped chamfer also extending for approximately 0.25 inch. A cylindrical surface 39 can be provided by, for example, leaving a portion of the exchange core wire material unground at a location proximal of the tapered stop 38. Tapered stop 38 typically would have a maximum length of on the order of about 0.375 inch.

A typical fixed wire tube 33 will have an outer diameter of about 0.018 inch or less, providing size and performance characteristics comparable to those of a standard guidewire used for inserting angioplasty catheters. A typical diameter of cylindrical surface 39 is 0.009 inch, while the internal diameter of the hypodermic tube 34 is slightly greater than this in order to accommodate the needed sliding movement between these two surfaces. The remaining cylindrical surface of the exchange core wire 35 for a device of this size is a diameter of about 0.0075 inch. Typically, the total length of the exchange core wire 35 is 50 inches, while the total length of the extendable balloon-on-a-wire catheter is about 300 cm, or about 118 inches. Exchange core wire 35 can be constructed, for example, of stainless steel or Nitinol alloy, the primary constituents of which are nickel and titanium.

Figure 3:
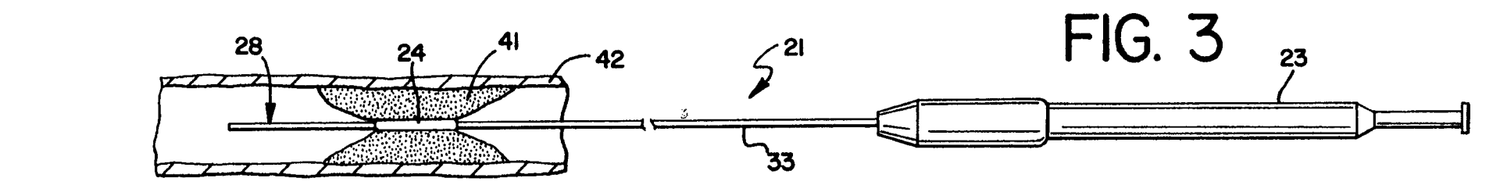
FIG. 3 is a broken-away elevational view of the extendable balloon-on-a-wire assembly as inserted, prior to inflation, into a vessel shown in cross-section.

With further reference to the balloon-on-a-wire catheter 21, it is sufficiently flexible to permit maneuvering through arterial branches and stenoses, while being sufficiently stiff to prevent folding or buckling of it and of catheters inserted over it. With reference to the distal portion of the balloon-on-a-wire catheter, it is designed to exhibit material thickness, strength, elasticity, inflation diameter and uninflated profile properties that are suitable for these types of devices. When inserted, typically through the arterial system or other body vessel passageway and to a stenosis or the like, the balloon 24 is in an uninflated state as illustrated in FIG. 3, which also illustrates a stenosis 41 within a vessel 42.

Figure 4:
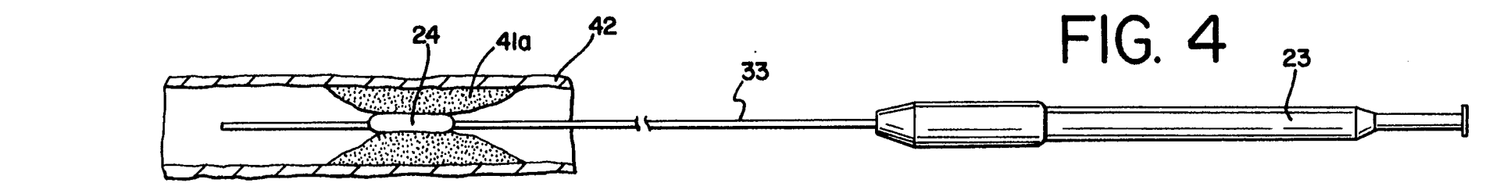
FIG. 4 shows the balloon-on-a-wire assembly inflated to perform an initial dilation, or to predilate, a stenosis of the vessel.
Figure 5:
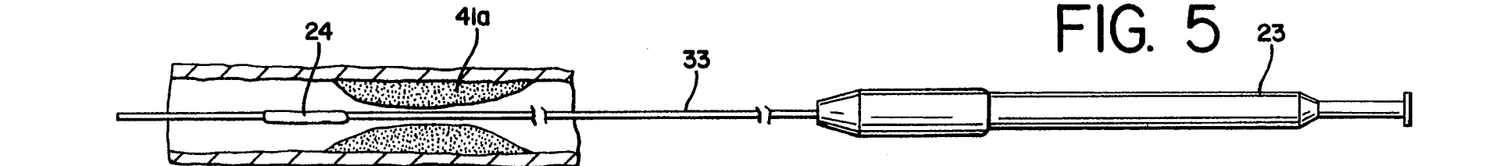
FIG. 5 illustrates the balloon-on-a-wire assembly moved distally of the predilated stenosis.

FIG. 4 illustrates inflation of the balloon 24 within the stenosis which is thereby opened somewhat, designated as 41a. The balloon is inflated with pressurized fluid passing through the steering device 23 and through the passageway 25. The pressurized fluid is usually an inert solution, such as a saline solution. Once the stenosis has been initially dilated or predilated with the balloon-on-a-wire catheter 21, the surgeon deflates the balloon 24, such as by drawing the inert fluid out through the steering device 23 in accordance with generally known procedures in order to thereby facilitate removal of the balloon 24 from the predilated stenosis 41a. FIG. 5 shows the device after balloon deflation and distally directed movement. It will be noted that the deflated balloon 24 itself is distal of the predilated stenosis.

Figure 6:
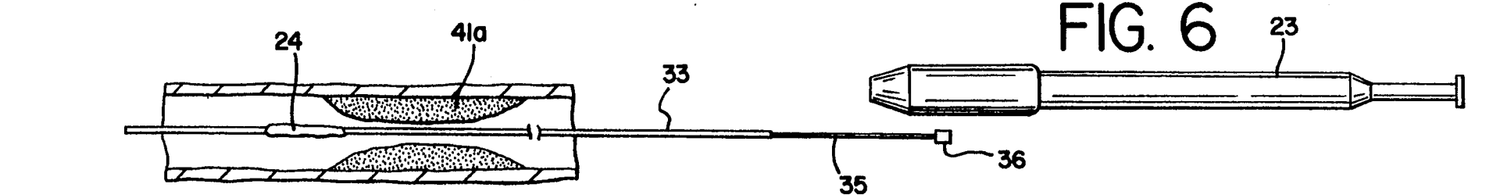
FIG. 6 illustrates the steering device of the balloon-on-a-wire assembly as detached from the remainder of the assembly.
Figure 7:
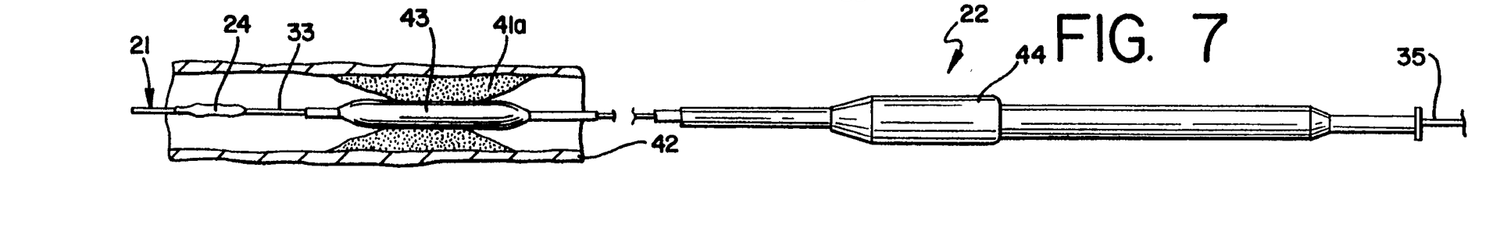
FIG. 7 is a broken-away elevational view illustrating an over-the-wire balloon catheter positioned over the extendable balloon-on-a-wire catheter after extension of the core wire therefrom.

FIG. 6 generally illustrates removal of the steering device 23 from the fixed wire tube 33. Steering device 23 is easily removed by simply pulling same off of the force fit connection illustrated in somewhat greater detail in FIG. 1. With the steering device removed, the surgeon is then free to pull the exchange core wire 35 out of the fixed wire tube 33, more specifically out of the hypodermic tube 34 therewithin, such as by grasping proximal end bead 36, when provided. FIG. 7 depicts insertion of an over-the-wire catheter 22 over the fixed wire tube 33 and/or the exchange core wire 35. Preferably, the length of the exchange core wire 35 is longer than the full length of the over-the-wire catheter 22 so the physician can maintain control of the position of the deflated balloon 24 distally of the stenosis such as by grasping the fixed wire tube 33 and/or the exchange core wire 35 at all times during sliding of the catheter 22 over the catheter 21, including the extended exchange core wire 35. FIG. 7 illustrates the completion of this insertion procedure. It will be noted that the over-the-wire catheter 22 has a balloon 43, illustrated operating upon the predilated stenosis 41a.

Catheter 22 itself has a hub or steering assembly 44 which accommodates the exchange core wire 35 during insertion and which has appropriate means, well known in the art, to perform as a manifold to communicate pressurized fluid through the catheter 22 and to the balloon 43. When the desired treatment has been completed, the catheter 22 may be first removed, followed by removal of the catheter 21, or both catheters can be removed together. It will be appreciated that the balloon-on-a-wire catheter 21 remains in place throughout the procedure until the surgeon decides to move same. In fact, once the catheter 21 is moved slightly distally as illustrated in FIG. 5, it remains substantially in place throughout the procedure, with its deflated balloon 24 positioned just distally of the lesion or stenosis. It will thus be appreciated that the balloon-on-a-wire catheter which also performs the function of a guidewire is inserted and removed only once during an entire procedure.

The combined length of the fixed wire tube 33 and the exchange core wire 35 is long enough to allow the over-the-wire catheter 22 to be completely removed from the patient while the distal end of the balloon-on-a-wire catheter continues to bridge the stenosis 41, when this approach is desired. Except in those situations where the interengagement between the diameter reduction area 37 of the hypodermic tube 34 and the tapered stop 38 of the exchange core wire 35 is substantially permanent due to deformation of these two components whereby they cannot be readily separated, the exchange core wire 35 can be pushed back into the balloon-on-a-wire catheter 21 and thus into the patient, and a replacement catheter can then be routed over the catheter 21 to position a balloon, for example, relative to the stenosis at the distal end portion of the extendable balloon-on-a-wire catheter 21.

With further reference to the procedure practiced in accordance with the present invention, the following illustrates an angioplasty procedure. The balloon-on-a-wire catheter is inserted through the patient's arterial system and to a stenosis in substantially the same manner as practiced for a standard guidewire. The profile of the catheter is generally the same as a standard guidewire, permitting comparable maneuverability in order to access the stenosis. The balloon-on-a-wire catheter is then inserted into the stenosis so that the deflated balloon is generally therewithin. Next, the balloon is inflated to predilate the stenosis, deflated to permit movement, and then pushed distally of the predilated stenosis.

Thereafter, the surgeon slides the over-the-wire balloon catheter over the balloon-on-a-wire catheter and to the predilated stenosis, without passing over the balloon of the balloon-on-a-wire catheter. Subsequent inflation and deflation of the balloon of the over-the-wire catheter further dilates the stenosis, usually completing the procedure. If needed, the surgeon may exchange this balloon catheter for a larger one or for another treatment device. This allows, for example, further dilation of the stenosis. Even in this event, the surgeon again leaves the balloon-on-a-wire catheter in place with its tip being distal of the stenosis during the procedure of guiding the larger balloon catheter to and through the stenosis.

It will be noted that the balloon of the balloon-on-a-wire catheter does not need to pass through the over-the-wire catheter or catheters. This permits one to utilize an over-the-wire catheter having a lumen of particularly small radial size. This can permit the use of an over-the-wire catheter having an outer diameter which is also correspondingly smaller, permitting insertion of same into tighter stenoses or vessels. This can permit the balloon-on-a-wire catheter to be structured such that it does not need to predilate the stenosis as widely as otherwise might be required for a larger sized over-the-wire catheter.

It will be understood that the embodiments of the present invention which have been described are illustrative of some of the applications of the principles of the present invention. Numerous modifications may be made by those skilled in the art without departing from the true spirit and scope of the invention.

I claim:

1. An extendable balloon-on-a-wire catheter, comprising:

a fixed wire percutaneous transluminal angioplasty balloon dilation catheter assembly which is a balloon-on-a-wire assembly having an elongated body with a proximal end portion and with a balloon member at a distal portion thereof, said elongated body being a wire-like member having an inside wall defining a lumen, said elongated body having an outer diameter substantially the same as that of a catheter guidewire;

an extension assembly longitudinally positioned within said lumen of the elongated body of the balloon-on-a-wire assembly, a longitudinally extending portion of said lumen of the elongated body defining an elongated passageway, said elongated passageway communicating pressurized fluid between said balloon member and said proximal end portion of the balloon-on-a-wire assembly; and said extension assembly includes a hypodermic tube secured within said balloon-on-a-wire assembly, said hypodermic tube having a proximal end and a distal end, said elongated passageway being between an exterior elongated surface of the hypodermic tube and said lumen of the elongated surface of the balloon-on-a-wire assembly, said extension assembly further including an exchange core wire slidably positioned within and extendable out of said hypodermic tube in the proximal direction, and said exchange core wire being prevented from extending out of said hypodermic tube in the distal direction.

2. The extendable catheter in accordance with claim 1, wherein a portion of said exterior elongated surface of the hypodermic tube is adhered to said inside wall of the elongated body of the balloon-on-a-wire assembly.

3. The extendable catheter in accordance with claim 2, wherein said exterior elongated surface and said inside wall are adhered together with a metal adhesive.

4. The extendable catheter in accordance with claim 1, wherein said hypodermic tube and said exchange core wire have a movement-limiting section which resists movement of the exchange core wire in a proximal direction.

5. The extendable catheter in accordance with claim 4, wherein said movement-limiting section includes a diameter reduction area of said hypodermic tube in combination with a stop member of said exchange core wire.

6. An extendable balloon-on-a-wire catheter, comprising:

a fixed wire percutaneous transluminal angioplasty balloon-dilation catheter assembly which is a balloon-on-a-wire assembly having an elongated body with the a proximal end portion and with a balloon member at a distal portion thereof, said elongated body being a wire-like member having an inside wall defining a lumen, said elongated body having an outer diameter substantially the same as that of a catheter guidewire;

an extension assembly longitudinally positioned within said lumen of the elongated body of the balloon-on-a-wire assembly, a longitudinally extending portion of said lumen of the elongated body defining an elongated passageway, said elongated passageway communicating pressurized fluid between said balloon member and said proximal end portion of the balloon-on-a-wire assembly;

said extension assembly includes a hypodermic tube secured within said balloon-on-a-wire assembly, said elongated passageway being between an exterior elongated surface of the hypodermic tube and said lumen of the elongated body of the balloon-on-a-wire assembly, said extension assembly further including an exchange core wire slidably positioned within and extendable out of said hypodermic tube; and p1 a movement-limiting section is positioned at a proximal end portion of the hypodermic tube and at a distal end portion of the exchange core wire.

7. An extendable balloon-on-a-wire catheter, comprising:

a fixed wire percutaneous transluminal angioplasty balloon dilation catheter assembly which is a balloon-on-a-wire assembly having an elongated body with a proximal end portion and with a balloon member at a distal portion thereof, said elongated body being a wire-like member having an inside wall defining a lumen, said elongated body having an outer diameter substantially the same as that of a catheter guidewire;

an extension assembly longitudinally positioned within said lumen of the elongated body of the balloon-on-a-wire assembly, a longitudinally extending portion of said lumen of the elongated body defining an elongated passageway, said elongated passageway communicating pressurized fluid between said balloon member and said proximal end portion of the balloon-on-a-wire assembly;

said extension assembly includes a hypodermic tube secured within said balloon-on-a-wire assembly, said elongated passageway being between an exterior elongated surface of the hypodermic tube and said lumen of the elongated body of the balloon-on-a-wire assembly, said extension assembly further including an exchange core wire slidably positioned within and extendable out of said hypodermic tube; and said hypodermic tube and said exchange core wire have a movement-limiting section which resists movement of the exchange core wire in a proximal direction, said movement-limiting section includes a diameter reduction area of said hypodermic tube in combination with a stop of said exchange core wire, said diameter reduction area is at a proximal end portion of the hypodermic tube, and said stop is at a distal end portion of the exchange core wire.

8. An extendable balloon-on-a-wire catheter, comprising:

a fixed wire percutaneous transluminal angioplasty balloon dilation catheter assembly which is a balloon-on-a-wire assembly having an elongated body with a proximal end portion and with a balloon member at a distal portion thereof, said elongated body being a wire-like member having an inside wall defining a lumen, said elongated body having an outer diameter substantially the same as that of a catheter guidewire;

an extension assembly longitudinally positioned within said lumen of the elongated body of the balloon-on-a-wire assembly, a longitudinally extending portion of said lumen of the elongated body defining an elongated passageway, said elongated passageway communicating pressurized fluid between said balloon member and said proximal end portion of the balloon-on-a-wire assembly;

said extension assembly includes a hypodermic tube secured within said balloon-on-a-wire assembly, said elongated passageway being between an exterior elongated surface of the hypodermic tube and said lumen of the elongated body of the balloon-on-a-wire assembly, said extension assembly further including an exchange core wire slidably positioned within and extendable out of said hypodermic tube; and said hypodermic tube and said exchange core wire have a movement-limiting section which resists movement of the exchange core wire in a proximal direction, and said movement-limiting section includes a gradually tapered frusto-conical stop surface of said exchange core wire and a reduced diameter tapered surface of said hypodermic tube, the taper of said hypodermic tube reduced diameter tapered surface being steeper than the taper of said frusto-conical stop surface.

9. The extendable catheter in accordance with claim 1, further including a steering device having a receptor opening at its distal portion which has a radial cross-section complementary in size and shape to a radial cross-section of a proximal end portion of said elongated body of the balloon-on-a-wire assembly, whereby said receptor opening holdingly receives said proximal portion of the elongated body.

10. A multiple component balloon catheter system, comprising:

a fixed wire percutaneous transluminal angioplasty balloon dilation catheter assembly which is a balloon-on-a-wire assembly having an elongated body with a proximal end portion and with a balloon member at a distal portion thereof, said elongated body being a wire-like member having an inside wall defining a lumen, said elongated body having an outer diameter substantially the same as that of a catheter guidewire; an extension assembly longitudinally positioned within said lumen of the elongated body of the balloon-on-a-wire assembly, an elongated passageway defined along said lumen and extending between said balloon member and said proximal end portion of the balloon-on-a-wire assembly, said elongated passageway communicating pressurized fluid between said balloon member and said proximal end portion; and said extension assembly includes a hypodermic tube secured within said balloon-on-a-wire assembly, said hypodermic tube having a proximal end and a distal end, said elongated passageway being between an exterior elongated surface of the hypodermic tube and said lumen of the elongated body of the balloon-on-a-wire assembly, said extension assembly further including an exchange core wire slidably positioned within and extendable out of said hypodermic tube in the proximal direction, and said exchange core wire being prevented from extending out of said hypodermic tube in the distal direction; and an over-the-wire percutaneous transluminal catheter, said over-the-wire catheter having an elongated body with a treatment member at a distal end portion thereof, said elongated body of the over-the-wire catheter being a tubular member having a lumen for communicating treatment fluid between a proximal end portion of the over-the-wire catheter and its said treatment member, said lumen of the over-the-wire catheter exhibiting an inner diameter which is slightly larger than said outer diameter of the elongated body of the balloon-on-a-wire assembly, whereby said over-the-wire catheter is slidably inserted over the elongated body of the balloon-on-a-wire assembly.

11. The multiple component catheter system in accordance with claim 10, wherein said inner diameter of the over-the-wire catheter is sized whereby the over-the-wire catheter is not slidable over said balloon member of the balloon-on-a-wire assembly.

12. The multiple component catheter system in accordance with claim 10, wherein said balloon-on-a-wire assembly includes a steering device at a proximal end of said elongated body thereof, said steering device being removable after insertion of the balloon-on-a-wire assembly within a living body vessel in order to gain access to a proximal end of the exchange core wire to permit its slidable extension out of said hypodermic tube and out of said elongated body of the balloon-on-a-wire assembly.

13. A multiple component balloon catheter system, comprising:

a fixed wire percutaneous transluminal angioplasty balloon dilation catheter assembly which is a balloon-on-a-wire assembly having an elongated body with a proximal end portion and with a balloon member at a distal portion thereof, said elongated body being a wire-like member having an inside wall defining a lumen, said elongated body having an outer diameter substantially the same as that of a catheter guidewire; an extension assembly longitudinally positioned within said lumen of the elongated body of the balloon-on-a-wire assembly, an elongated passageway defined along said lumen and extending between said balloon member and said proximal end portion of the balloon-on-a-wire assembly, said elongated passageway communicating pressurized fluid between said balloon member and said proximal end portion; and said extension assembly includes a hypodermic tube secured within said balloon-on-a-wire assembly, said elongated passageway being between an exterior elongated surface of the hypodermic tube and said lumen of the elongated body of the balloon-on-a-wire assembly, said extension assembly further including an exchange core wire slidably positioned within and extendable out of said hypodermic tube; and an over-the-wire percutaneous transluminal catheter, said over-the-wire catheter having an elongated body with a treatment member at a distal end portion thereof, said elongated body of the over-the-wire catheter being a tubular member having a lumen for communicating treatment fluid between a proximal end portion of the over-the-wire catheter and its said treatment member, said lumen of the over-the-wire catheter exhibiting an inner diameter which is slightly larger than said outer diameter of the elongated body of the balloon-on-a-wire assembly, and said inner diameter of the lumen of the over-the-wire catheter body is smaller than the external sizing of said balloon of the balloon-on-a-wire assembly when said balloon is deflated.

14. The multiple component catheter in accordance with claim 10, wherein a portion of said exterior elongated surface of the hypodermic tube is adhered to said inside wall of the elongated body of the balloon-on-a-wire assembly.

15. The multiple component catheter in accordance with claim 10, wherein said hypodermic tube and said exchange core wire have a movement-limiting section which resists movement of the exchange core wire in a proximal direction.

16. The multiple component catheter in accordance with claim 14, wherein said movement-limiting section includes a diameter reduction area of said hypodermic tube in combination with a stop member of said exchange core wire.

17. A multiple component balloon catheter system, comprising;
a fixed wire percutaneous transluminal angioplasty balloon dilation catheter assembly which is a balloon-on-a-wire assembly having an elongated body with a proximal end portion and with a balloon member at a distal portion thereof, said elongated body being a wire-like member having an inside wall defining a lumen, said elongated body having an outer diameter substantially the same as that of a catheter guidewire; an extension assembly longitudinally positioned within said lumen of the elongated body of the balloon-on-a-wire assembly, an elongated passageway defined along said lumen and extending between said balloon member and said proximal end portion of the balloon-on-a-wire assembly, said elongated passageway communicating pressurized fluid between said balloon member and said proximal end portion; and said extension assembly includes a hypodermic tube secured within said balloon-on-a-wire assembly, said elongated passageway being between an exterior elongated surface of the hypodermic tube and said lumen of the elongated body of the balloon-on-a-wire assembly, said extension assembly further including an exchange core wire slidably positioned within and extendable out of said hypodermic tube;

an over-the-wire percutaneous transluminal catheter, said over-the-wire catheter having an elongated body with a treatment member at a distal end portion thereof, said elongated body of the over-the-wire catheter being a tubular member having a lumen for communicating treatment fluid between a proximal end portion of the over-the-wire catheter and its said treatment member, said lumen of the over-the-wire catheter exhibiting an inner diameter which is slightly larger than said outer diameter of the elongated body of the balloon-on-a-wire assembly, whereby said over-the-wire catheter is slidably inserted over the elongated body of the balloon-on-a-wire assembly; and said hypodermic tube and said exchange core wire have a movement-limiting section which resists movement of the exchange core wire in a proximal direction, and said movement-limiting section is positioned at a proximal end portion of the hypodermic tube and at a distal end portion of the exchange core wire.

18. A multiple component balloon catheter system, comprising:
a fixed wire percutaneous transluminal angioplasty balloon dilation catheter assembly which is a balloon-on-a-wire assembly having an elongated body with a proximal end portion and with a balloon member at a distal portion thereof, said elongated body being a wire-like member having an inside wall defining a lumen, said elongated body having an outer diameter substantially the same as that of a catheter guidewire; and extension assembly longitudinally positioned within said lumen of the elongated body of the balloon-on-a-wire assembly, an elongated passageway defined along said lumen and extending between said balloon member and said proximal end portion of the balloon-on-a-wire assembly, said elongated passageway communicating pressurized fluid between said balloon member and said proximal end portion; and said extension assembly includes a hypodermic tube secured within said balloon-on-a-wire assembly, said elongated passageway being between an exterior elongated surface of the hypodermic tube and said lumen of the elongated body of the balloon-on-a-wire assembly, said extension assembly further including an exchange core wire slidably positioned within sand extendable out of said hypodermic tube;

an over-the-wire percutaneous transluminal catheter, said over-the-wire catheter having an elongated body with a treatment member at a distal end portion thereof, said elongated body of the over-the-wire catheter being a tubular member having a lumen for communicating treatment fluid between a proximal end portion of the over-the-wire catheter and its said treatment member, said lumen of the over-the-wire catheter exhibiting an inner diameter which is slightly larger than said outer diameter of the elongated body of the balloon-on-a-wire assembly, whereby said over-the-wire catheter is slidably inserted over the elongated body of the balloon-on-a-wire assembly; and said hypodermic tube and said exchange core wire have a movement-limiting section which resists movement of the exchange core wire in a proximal direction, said movement-limiting section includes a diameter reduction area of sad hypodermic tube in combination with a stop of said exchange core wire, and said diameter reduction area is at a proximal end portion of the hypodermic tube, and said stop is at a distal end portion of the exchange core wire.

19. A multiple component balloon catheter system, comprising:

a fixed wire percutaneous transluminal angioplasty balloon dilation catheter assembly which is a balloon-on-a-wire assembly having an elongated body with a proximal end portion and with a balloon member at a distal portion thereof, said elongated body being a wire-like member having an inside wall defining a lumen, said elongated body having an outer diameter substantially the same as that of a catheter guidewire; an extension assembly longitudinally positioned within said lumen of the elongated body of the balloon-on-a-wire assembly, an elongated passageway defined along said lumen and extending between said balloon member and said proximal end portion of the balloon-on-a-wire assembly, said elongated passageway communicating pressurized fluid between said balloon member and said proximal end portion; and said extension assembly includes a hypodermic tube secured within said balloon-on-a-wire assembly, said elongated passageway being between an exterior elongated surface of the hypodermic tube and said lumen of the elongated body of the balloon-on-a-wire assembly, said extension assembly further including an exchange core wire slidably positioned within and extendable out of said hypodermic tube;

an over-the-wire percutaneous transluminal catheter, said over-the-wire catheter having an elongated body with a treatment member at a distal end portion thereof, said elongated body of the over-the-wire catheter being a tubular member having a lumen for communicating treatment fluid between a proximal end portion of the over-the-wire catheter and its said treatment member, said lumen of the over-the-wire catheter exhibiting an inner diameter which is slightly larger than said outer diameter of the elongated body of the balloon-on-a-wire assembly, whereby said over-the-wire catheter is slidably inserted over the elongated body of the balloon-on-a-wire assembly; and said hypodermic tube and said exchange core wire have a movement-limiting section which resists movement of the exchange core wire in a proximal direction, and said movement-limiting section includes a gradually tapered frusto-conical stop surface of said exchange core wire and a reduced diameter tapered surface of said hypodermic tube, the taper of said hypodermic tube reduced diameter tapered surface being steeper than the taper of said frusto-conical stop surface.

20. A transluminal percutaneous procedure for treating a stenosis and the like within a living body vessel, comprising the steps of:

inserting into a living body vessel a fixed wire percutaneous transluminal angioplasty balloon dilation catheter which is a balloon-on-a-wire assembly having an elongated body with a balloon member at a distal end portion thereof and having a steering device at a proximal end portion thereof;

locating the balloon member within a stenosis of the living body vessel, inflating the balloon member to predilate the stenosis, and deflating the balloon member;

moving the balloon-on-a-wire assembly distally within the body vessel to a location such that the balloon member is closely distally spaced from the stenosis which has been predilated;

removing the steering device from the proximal end portion of the balloon-on-a-wire assembly in order to gain access to an exchange core wire telescopingly positioned within the elongated body of the balloon-on-a-wire assembly;

slidably inserting an over-the-wire percutaneous transluminal catheter into the body vessel and over the elongated body of the balloon-on-a-wire assembly until the over-the-wire catheter is located at the stenosis which had been predilated;

treating the predilated stenosis by manipulation of the over-the-wire catheter;

removing the over-the-wire catheter from the body vessel; and removing the balloon-on-a-wire assembly from the body vessel.

21. The procedure in accordance with claim 20, wherein said step of removing the over-the-wire catheter is preceded by extending the exchange core wire in a telescoping manner from out of the elongated body of the balloon-on-a-wire assembly, said telescopic extension step including extending the exchange core wire to have a length, when combined with a proximal portion of the elongated body of the balloon-on-a-wire assembly that is outside of the body, which is longer than the length of the proximal portion of the over-the-wire catheter, thereby permitting grasping of the proximal portion of the balloon-on-a-wire catheter and/or its extended exchange core wire during the entirety of said step of slidably inserting the over-the-wire catheter.

22. The procedure in accordance with claim 20, wherein said slidably inserting step is carried out without passing any portion of the over-the-wire catheter over the balloon member of the balloon-on-a-wire assembly.

23. The procedure in accordance with claim 20, wherein said slidably inserting step includes preventing passage of the over-the-wire catheter over the balloon member of the balloon-on-a-wire assembly by relative sizing of a lumen of the over-the-wire catheter and of the balloon member of the balloon-on-a-wire assembly whereby the balloon member will not pass through the lumen, even when the balloon member is deflated.

* * * * *

UNITED STATES PATENT AND TRADEMARK OFFICE
CERTIFICATE OF CORRECTION

PATENT NO. : 5,338,301
DATED : August 16, 1994
INVENTOR(S) : Juan-Carlos Diaz

It is certified that error appears in the above-indentified patent and that said Letters Patent is hereby corrected as shown below:

```
Col. 8, lines 2-3, "elongated surface" should read
      --elongated body--; line 30, "balloon-dilation"
      should read --balloon dilation--; line 54, delete
      --and pl--.
Col. 11, line 53, "14" should read --15--.
Col. 12, line 48, "and" should read --an--; line 64,
      "sand" should read --and--.
```

Signed and Sealed this

Twenty-sixth Day of September, 1995

Attest:

BRUCE LEHMAN

*Attesting Officer*      *Commissioner of Patents and Trademarks*